United States Patent [19]

Simon et al.

[11] Patent Number: 5,049,152
[45] Date of Patent: Sep. 17, 1991

[54] HEMOSTATIC CLIP APPLICATOR

[75] Inventors: Denise M. Simon, Harbor Springs, Mich.; Darren Saravis, Long Beach, Calif.

[73] Assignee: Richard-Allan Medical Industries, Richland, Mich.

[21] Appl. No.: 319,664

[22] Filed: Mar. 7, 1989

[51] Int. Cl.⁵ ............................................. A61B 17/12
[52] U.S. Cl. ..................................... 602/143; 606/139; 606/142; 227/19; 227/121
[58] Field of Search ....................... 606/139, 142, 143; 227/19, 121

[56] References Cited

U.S. PATENT DOCUMENTS

| | | |
|---|---|---|
| 4,043,504 | 8/1977 | Hueil et al. . |
| 4,152,920 | 5/1979 | Green . |
| 4,242,902 | 1/1981 | Green . |
| 4,296,751 | 10/1981 | Blake, III et al. . |
| 4,299,224 | 11/1981 | Noiles . |
| 4,316,468 | 2/1982 | Klieman et al. . |
| 4,325,376 | 4/1982 | Klieman et al. . |
| 4,410,125 | 10/1983 | Noiles et al. . |
| 4,412,539 | 11/1983 | Jarvik . |
| 4,425,915 | 1/1984 | Ivanov ............................... 227/19 X |
| 4,430,997 | 2/1984 | DiGiovanni et al. . |
| 4,452,357 | 6/1984 | Klieman et al. . |
| 4,452,376 | 6/1984 | Klieman et al. . |
| 4,471,780 | 9/1984 | Menges et al. . |
| 4,478,220 | 10/1984 | DiGiovanni et al. . |
| 4,480,641 | 11/1984 | Failla et al. . |
| 4,509,518 | 4/1985 | McGarry et al. ..................... 606/143 |
| 4,512,345 | 4/1985 | Green . |
| 4,522,207 | 6/1985 | Klieman et al. . |
| 4,534,351 | 8/1985 | Rothfuss et al. . |
| 4,549,544 | 10/1985 | Favaron . |
| 4,557,263 | 12/1985 | Green . |
| 4,572,183 | 2/1986 | Juska . |
| 4,576,166 | 3/1986 | Montgomery et al. .............. 606/143 |
| 4,598,711 | 7/1986 | Deniega . |
| 4,611,595 | 9/1986 | Klieman et al. . |
| 4,616,650 | 10/1986 | Green et al. . |
| 4,624,254 | 11/1986 | McGarry et al. . |
| 4,674,504 | 6/1987 | Klieman et al. . |
| 4,691,853 | 9/1987 | Storace . |
| 4,712,549 | 12/1987 | Peters et al. . |

Primary Examiner—Robert A. Hafer
Assistant Examiner—Kerry Owens
Attorney, Agent, or Firm—Neuman, Williams, Anderson & Olson

[57] ABSTRACT

The present invention relates to an improved reciprocating jaw type hemostatic clip applier or ligator. The improved apparatus is provided with an improved camming mechanism which interfaces with the jaws to cam the jaws closed and which is designed to maintain its alignment with respect to the jaws to prevent misalignment of the jaws during closure and malformation of clips. The improved apparatus is also provided with a lockout mechanism which prevents the jaws from being closed once the last clip has been formed and released from the instrument.

22 Claims, 12 Drawing Sheets

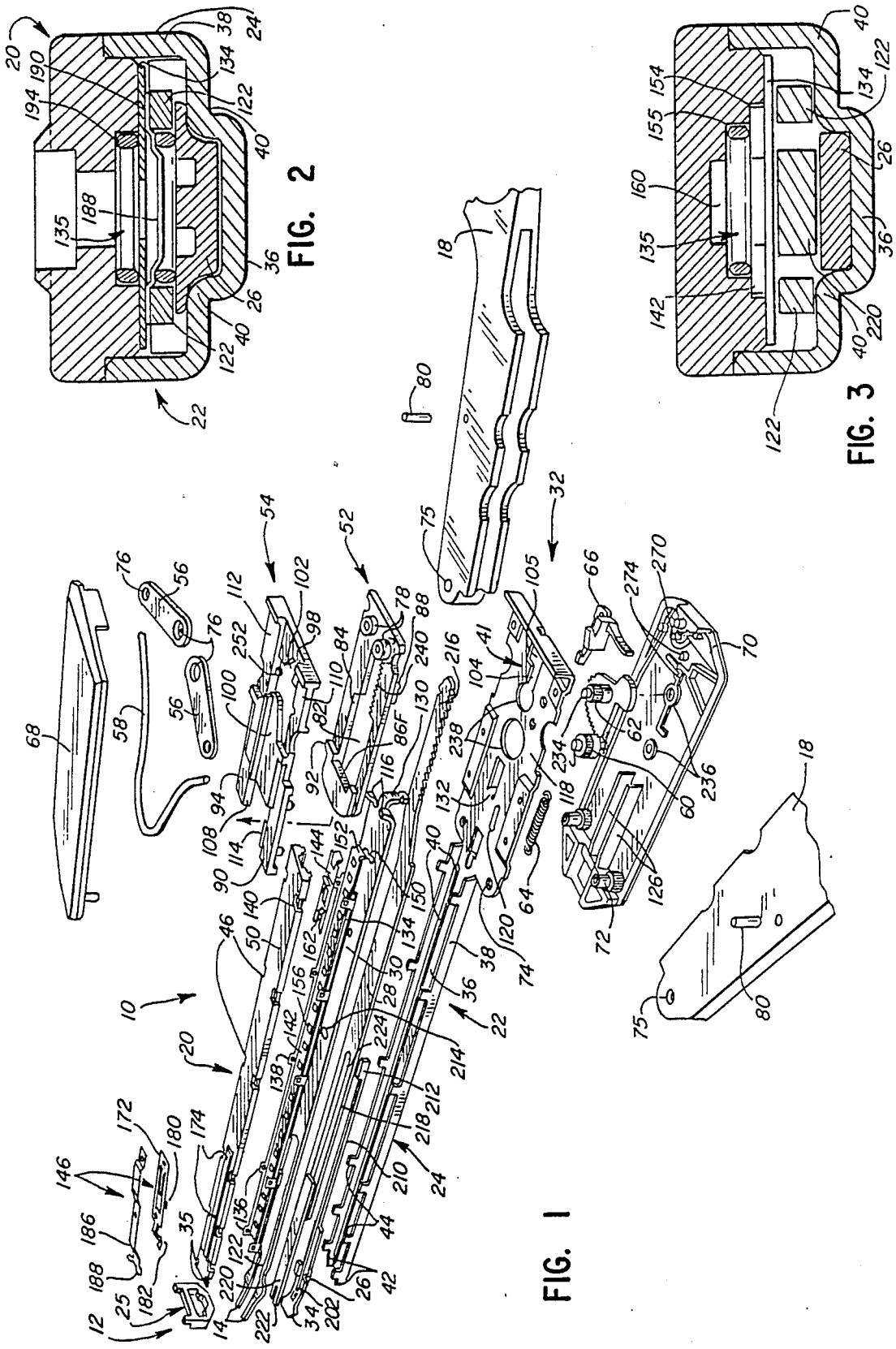

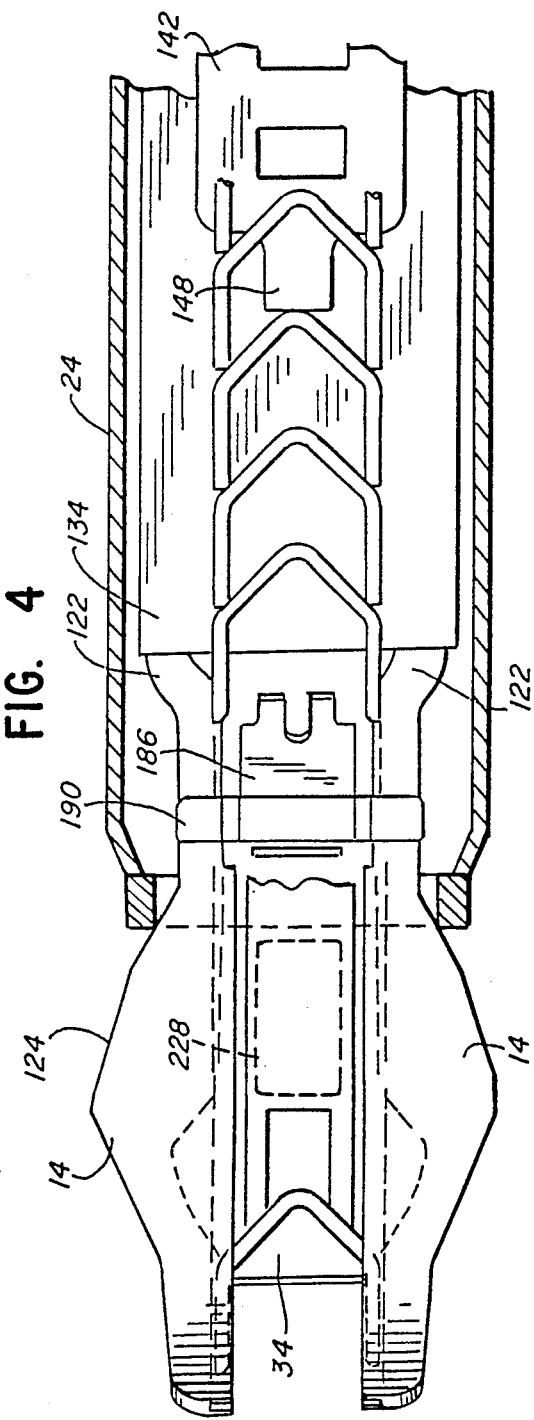
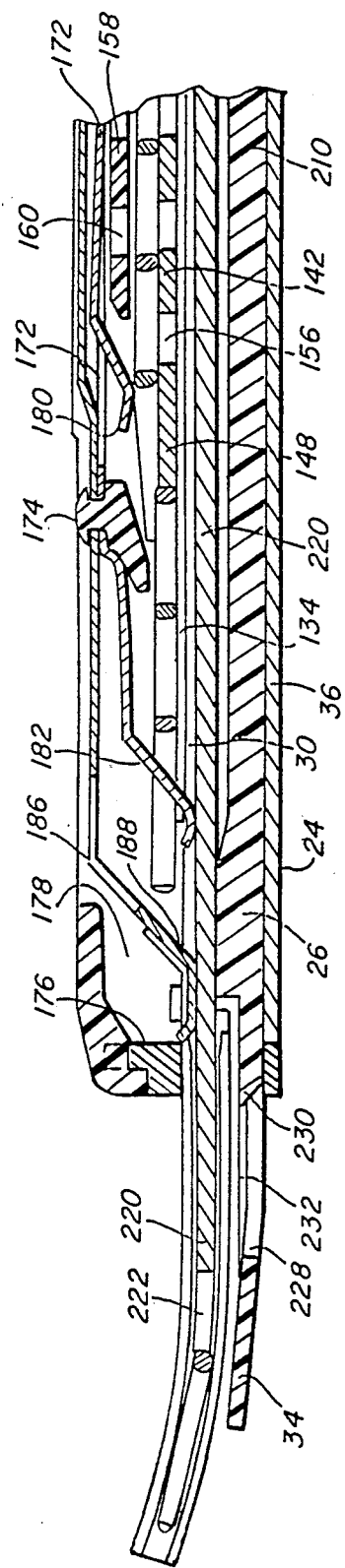
FIG. 4
FIG. 5

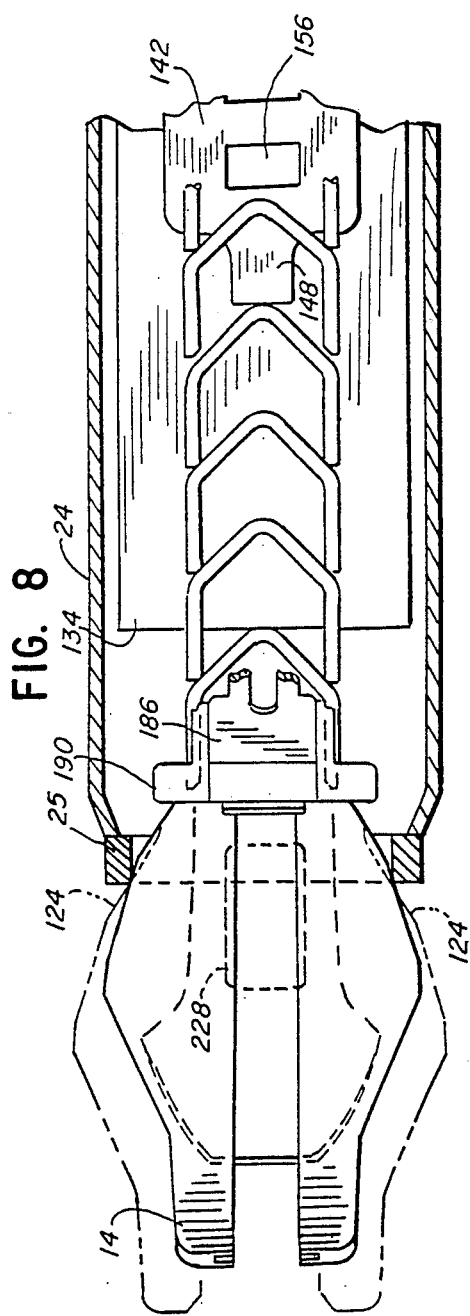
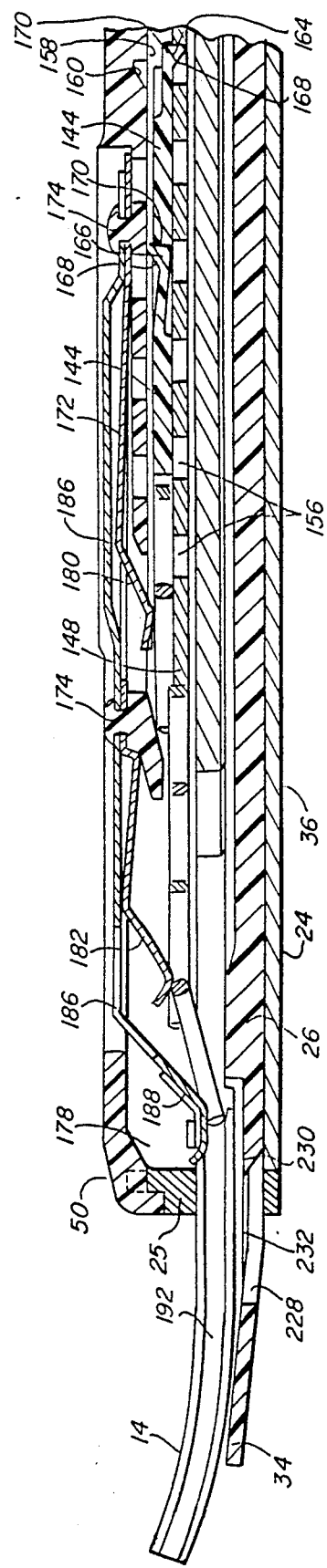
FIG. 8
FIG. 9

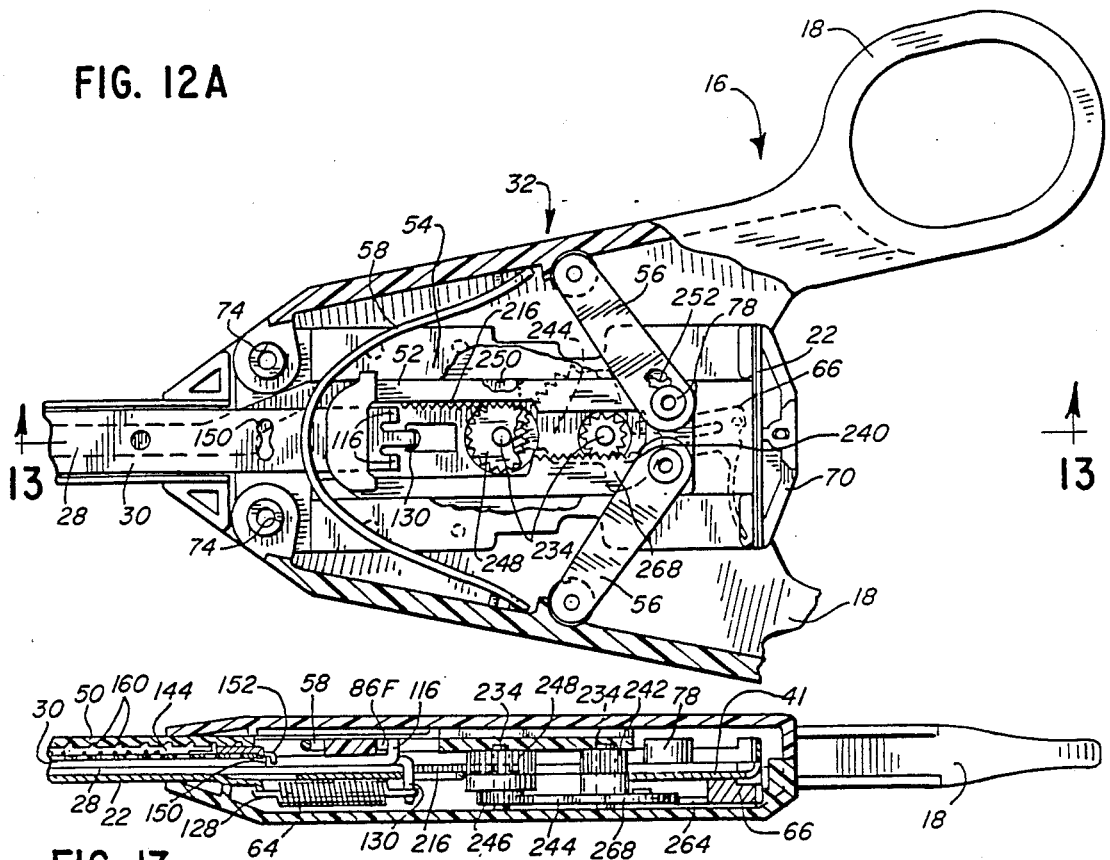
FIG. 12A
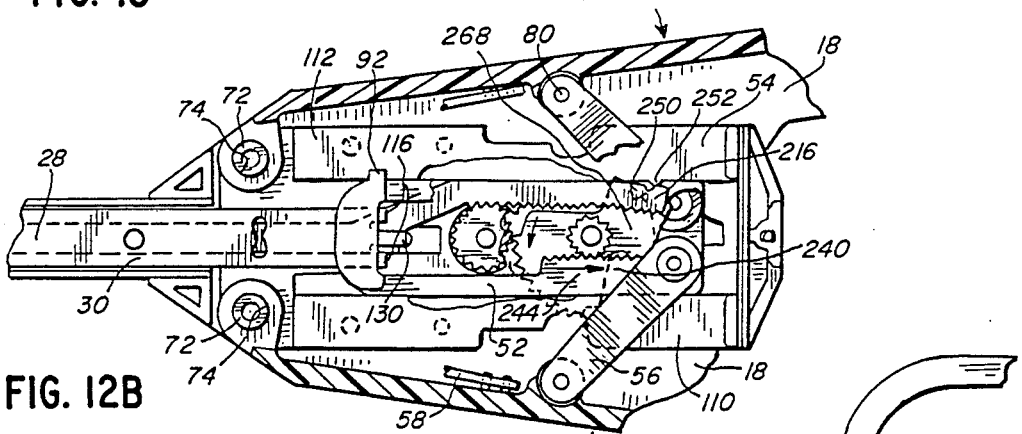
FIG. 13
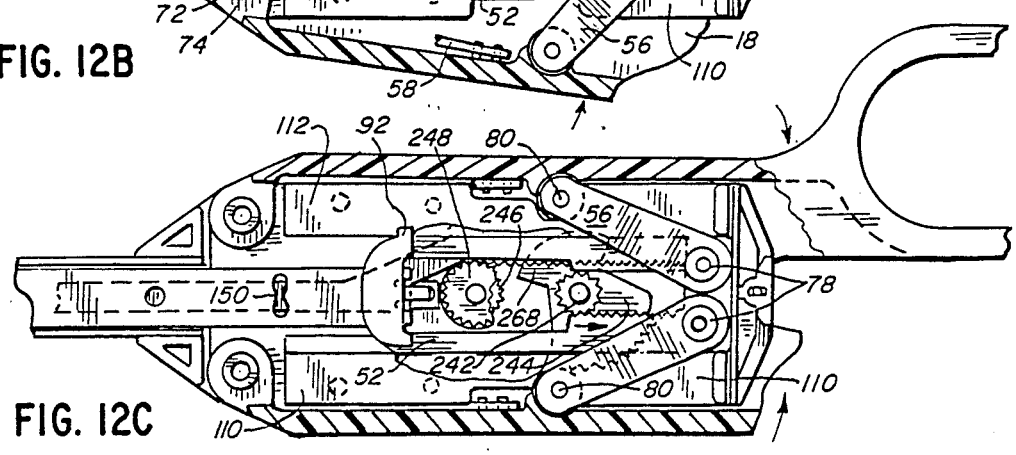
FIG. 12B
FIG. 12C

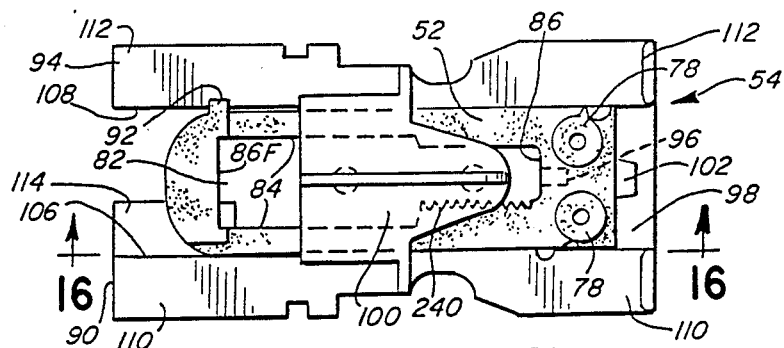
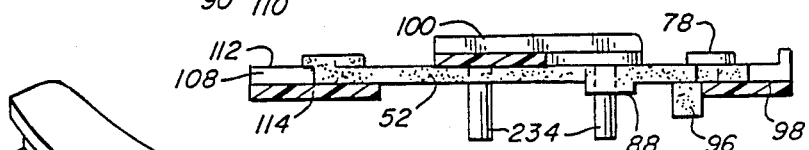
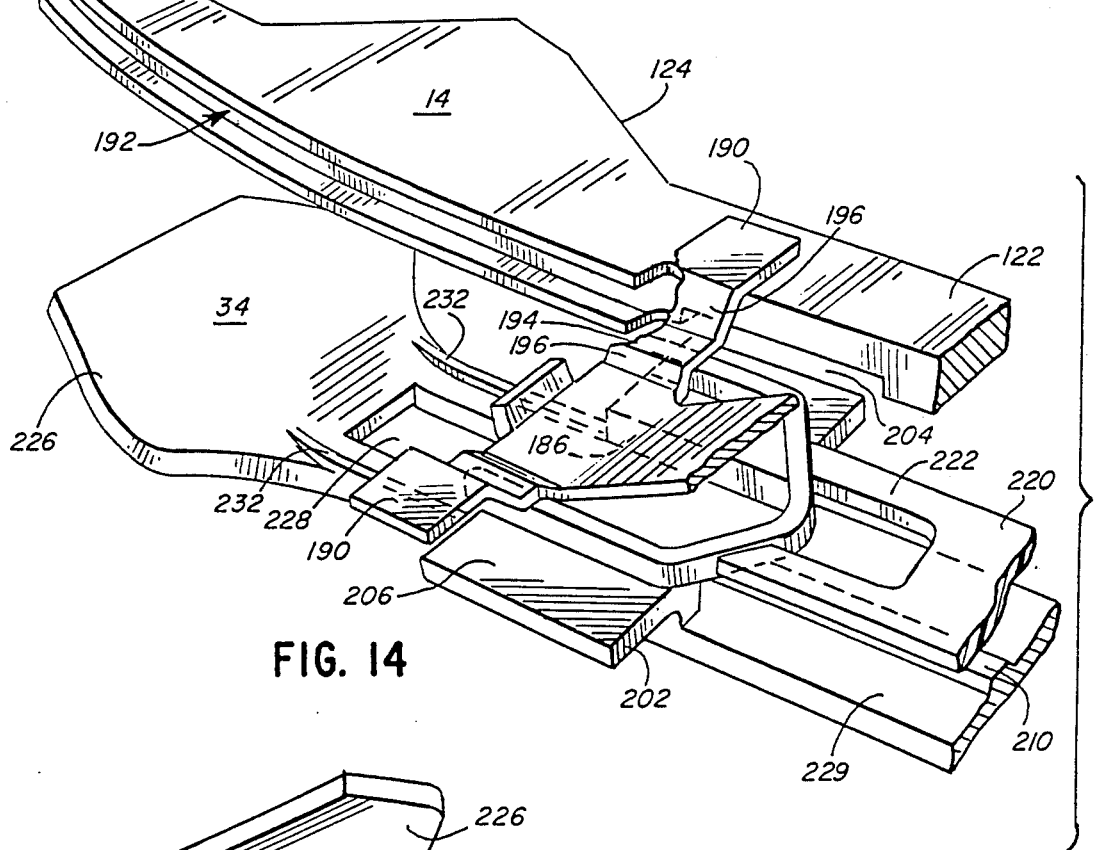
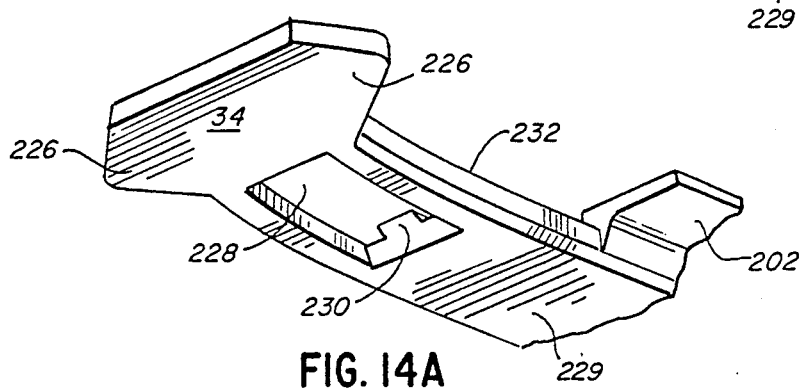

HEMOSTATIC CLIP APPLICATOR

FIELD OF THE INVENTION

The present invention relates to an improved surgical clip applicator for applying multiple surgical clips to body tissue or blood vessels as necessary during surgical procedures. In particular, the present invention is an improvement of the clip applier described in a pending U.S. patent application, Ser. No. 035074, assigned to Richard-Allan Medical Industries, Inc. The clip applicator described in that patent stores multiple clips, avoiding reloading after application of a clip, and automatically advances the clips to the instrument jaws after placement of each successive clip. Surgical clips are applied to blood vessels, veins, arteries or tissue prior to being severed or cut as required during surgery. In this manner, the loss of blood through the severed vessel is prevented and the flow of blood into the area where the surgeon is operating is also prevented.

In particular, the improved applicator contains a final lockout mechanism to prevent the jaws of the applicator from closing after the last clip has been formed. It also contains an improved camming surface or anti-distortion member to prevent the camming action of the jaws on the front end of the chassis of the applicator from distorting the chassis and thereby distorting the manner in which the jaws close.

DESCRIPTION OF THE PRIOR ART

Many methods of constricting blood vessels and the like have been employed over the years. These include pliers or scissors type instruments which are themselves clamped about a vessel as well as the use of small clamps applied to a vessel by a clamp applying instrument. These clamps have ranged widely in shape and size as well as in the manner in which they attach to and constrict a blood vessel.

Generally, there are two types of instruments for applying separate, individual clamping elements or clips to a blood vessel. The first type can be generally referred to as a scissors type because it consists of two arms having jaws at one end and handles at the opposite end with the arms pivotally connected near the jaw end. The instrument is activated similar to a pair of scissors; moving the handles together causes the jaws to clinch and separating the handles causes the jaws to open.

The second type of clip applicator applies camming principles rather than pivoting to clinch the jaws and deform a clip. Camming is achieved by either reciprocating the jaws within an exterior sleeve or reciprocating the sleeve about stationary jaws. In particular, the jaws can move rearward into the sleeve or the sleeve can move forward past the jaws to accomplish closing of the jaws and clinching of the clip. In either case, a camming action between the outside surface of the jaws and the forward edge of the sleeve close the jaws. This second type of clip applicator is manufactured in both single count or "one shot" versions or in multiple count versions. Moreover, given the present state of medical technology, these instruments are constructed primarily from plastic in order to produce a low cost instrument which justifies disposal after the single use. Of course, conventional clip appliers as well as the present invention could easily be manufactured from all metal componentry in order to be capable of sterilization and, therefore, reuse. The instrument of the present invention has reciprocating jaws within a stationary sleeve and houses multiple clips. The preferred embodiment is intended to be disposable.

The present invention improves upon the overall design and function of reciprocating jaw type clip applicators. Specifically, the present invention incorporates an anti-distortion member or ring, an improved camming surface which is located at the distal end of the forward portion of the chassis. The jaws engage the anti-distortion ring, rather than the chassis, and the contact causes the jaws to be cammed closed.

In prior reciprocating jaw type clip applicators, the jaws are cammed closed by the inside surfaces of the front portion of the chassis. The interaction of the jaws with the chassis forces the jaws to close around the clip being formed. As the jaws continue to form clips, the front portion of the chassis begins to distort under the repetitive action of the jaws acting against the camming surfaces located inside the front portion of the chassis. Distortion of the chassis, at this point, leads to non-uniform closure of the jaws which, in turn, leads to improper clip formation.

When clips are improperly formed they may not completely close. However, a surgeon will not know that a clip is partially open until after the blood vessel, about which the clip is formed, is severed. In that instance, blood will immediately begin flowing into the surgery site requiring the operation be delayed while the critical vessel is located and reclamped. Depending on the type and location of the surgery, locating the vessel may be difficult and the time delay could cause medical complications to the patient. The anti-distortion member or improved camming surface of the present invention solves the problems of clip malformation previously attributable to distortion of the chassis.

The present invention also improves upon the prior art by providing a final lock-out mechanism which prevents jaws closure after the final clip has been used. In prior clip applicators, once the last clip had been formed and released from the jaws of the instrument, there was no positive mechanism to inform the surgeon or nurse that the last clip had been used. The lack of a final lock-out allowed continued opening and closing of the jaws when there were no clips left to apply. Thus, the unwary surgeon could inadvertently close the jaws around an artery or vein possibly damaging or even completely severing the artery or vein.

OBJECTS OF THE INVENTION

It is general object of the present invention to provide an improved multiple count clip applicator for use during surgery.

It is a still further object of the present invention to provide a reciprocating jaw type clip applicator in which the jaws close uniformly and consistently throughout the life of the instrument.

It is another object of the present invention to provide an improved clip applicator which maintains proper clip formation throughout the applicator's useful life by preventing chassis distortion which can result from jaw opening and closing.

It is another object of the present invention to provide a signal to the surgeon after the last clip has been formed and released.

It is a still further object of the present invention to provide a lockout mechanism to prevent actuation of the clip applier after the last clip has been released from the instrument jaws.

Other objects and advantages of the invention will become apparent upon reading the following detailed description and appended claims and upon reference to the accompanying drawings.

DESCRIPTION OF THE DRAWINGS

FIG. 1 is an exploded perspective view of the present invention.

FIG. 2 is a cross sectional view of the present invention taken along line 2—2 of FIG. 10.

FIG. 3 is a cross sectional view of the present invention taken along line 3—3 of FIG. 6.

FIG. 4 is a partial top cross sectional view of the present invention as depicted in FIG. 5.

FIG. 5 is a side cross-sectional view of the present invention in an at rest position with the jaws fully opened and a clip loaded between the jaws.

FIG. 8 is a partial top view of the instrument shown in FIG. 9.

FIG. 9 is a side cross-sectional view of the present invention returning to an unactuated position with the jaws slightly open and the clips being advanced.

FIG. 12A is a partial top view of the actuating mechanism of the present invention in an at rest position with the handles fully open.

FIG. 12B is a partial top view of the present invention showing the handles partially closed with the ram and drawbar extension moving rearward.

FIG. 12C is a partial top view of the present invention showing the handles fully closed.

FIG. 13 is a side cross sectional view of the actuating or transmission mechanism of the present invention.

FIG. 14 is a partial perspective view of the forward end of the instrument of the present invention showing a clip positioned on the clip load platform ready for advancement into the jaws.

FIG. 14A is a partial bottom perspective view of the clipboard platform and tissue stop.

FIG. 15 is a top view of the gear housing and drawbar extension.

FIG. 16 is a side view of the gear housing and drawbar extension taken along line 16—16 of FIG. 15.

SUMMARY OF THE INVENTION

Figure 6:
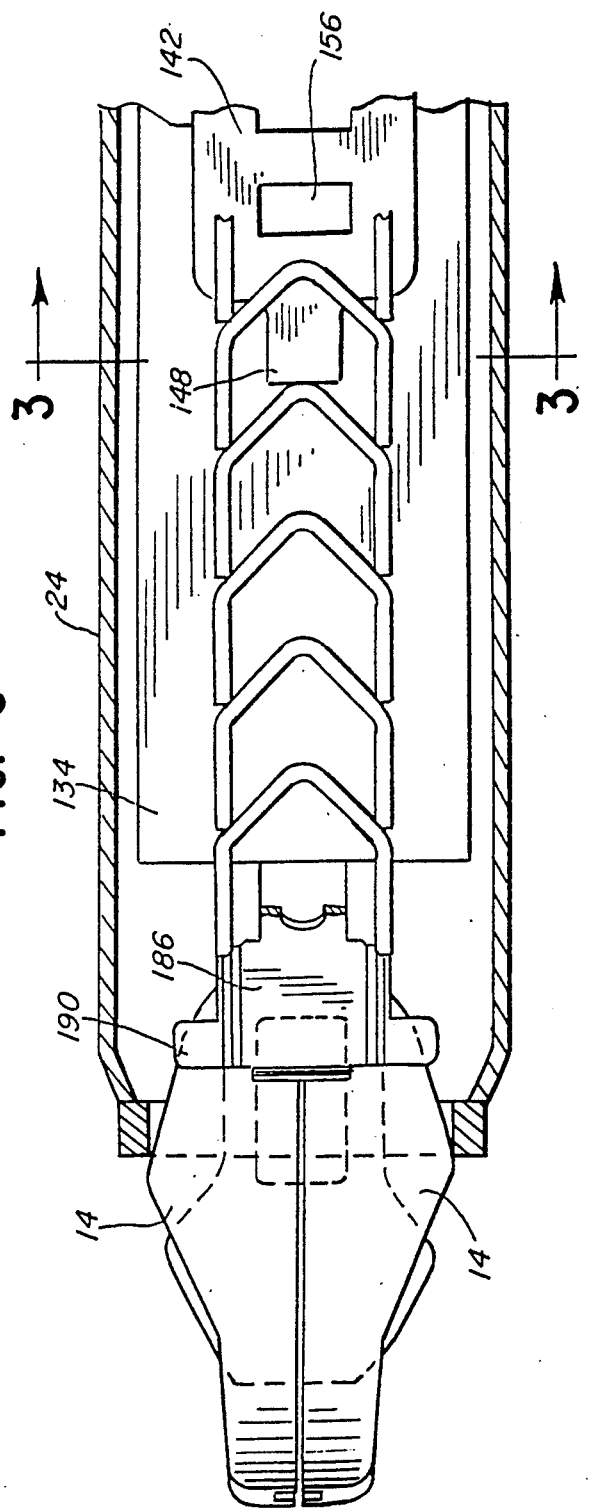
FIG. 6 is a partial top view of the present invention as shown in FIG. 7.

The present invention relates to an improved multiple count clip applier for applying surgical clips to blood vessels, veins or arteries to occlude the flow of blood. The clip applier of the present invention employs a transmission mechanism which translates the radial or arcuate closure of the instrument handles into linear or reciprocable movement of the jaws. By closing the instrument handles, the jaws of the present invention are retracted into a chassis or main body and cammed closed to deform a clip positioned between the jaws. Upon release of the handles the forwardmost clip in the clip housing is advanced and positioned between the jaws.

Proper clip formation is effected, in part, by the jaws being accurately cammed closed. Thus, the camming action must occur consistently from one clip to the next. However, continued opening and closing of the jaws results in distortion of the front end of the instrument which acts as the camming member to close the jaws. The present invention provides accurate jaw closure by absolutely maintaining the contour and shape of the front end of the instrument through the use of an anti-distortion member.

The anti-distortion member or ring, an improved camming surface, has been added to the front-portion of the chassis at the point where the jaws are cammed closed. The ring, provides a structural strength which the open ended chassis itself can not provide. As the jaws are retracted, the ring provides the camming surface for the jaws instead of the front portion of the chassis. Since the ring maintains its shape throughout the life of the instrument, which the chassis could not, the jaws are consistently closed and all of the clips are now consistently formed. This proper clip formation insures that arteries, blood vessels, and veins are properly clamped shut during the course of surgical procedure.

The present invention also improves surgical technique by incorporating a final lock-out mechanism in a multiple count clip applier. The final lock-out mechanism prevents inadvertent injury to veins and arteries by making sure the jaws cannot be closed once the final clip has been formed and released from the instrument. This improvement is accomplished by advancing the pawl to a position which effectively jams the instrument preventing closure of the handles and jaws.

DETAILED DESCRIPTION OF THE INVENTION

The relationship and workings of the various elements of the invention will be better understood by the following detailed description. However, the embodiment of the invention described below is by way of example only and applicants do not limit themselves to the embodiment. Furthermore one should understand that the drawings are not to scale and that the embodiments are illustrated by graphic symbols and fragmentary views. In certain instances, the applicant may have omitted details which are not necessary for an understanding of the present invention such as conventional details of fabrication and assembly.

When the clip applicator of the present invention is in an unactuated position, a clip is loaded in the jaw and the instrument is ready for use. Clip deformation occurs upon closure of the instrument handles and clip feed to the jaws occurs upon opening of the instrument handles. With the clip in place and ready for deformation, the surgeon can instantaneously place the instrument in position and deform the forwardmost clip about a blood vessel without experiencing any delay associated with having to first advance the clip to the jaws. As a result, the instrument is always ready for use.

Figure 17:
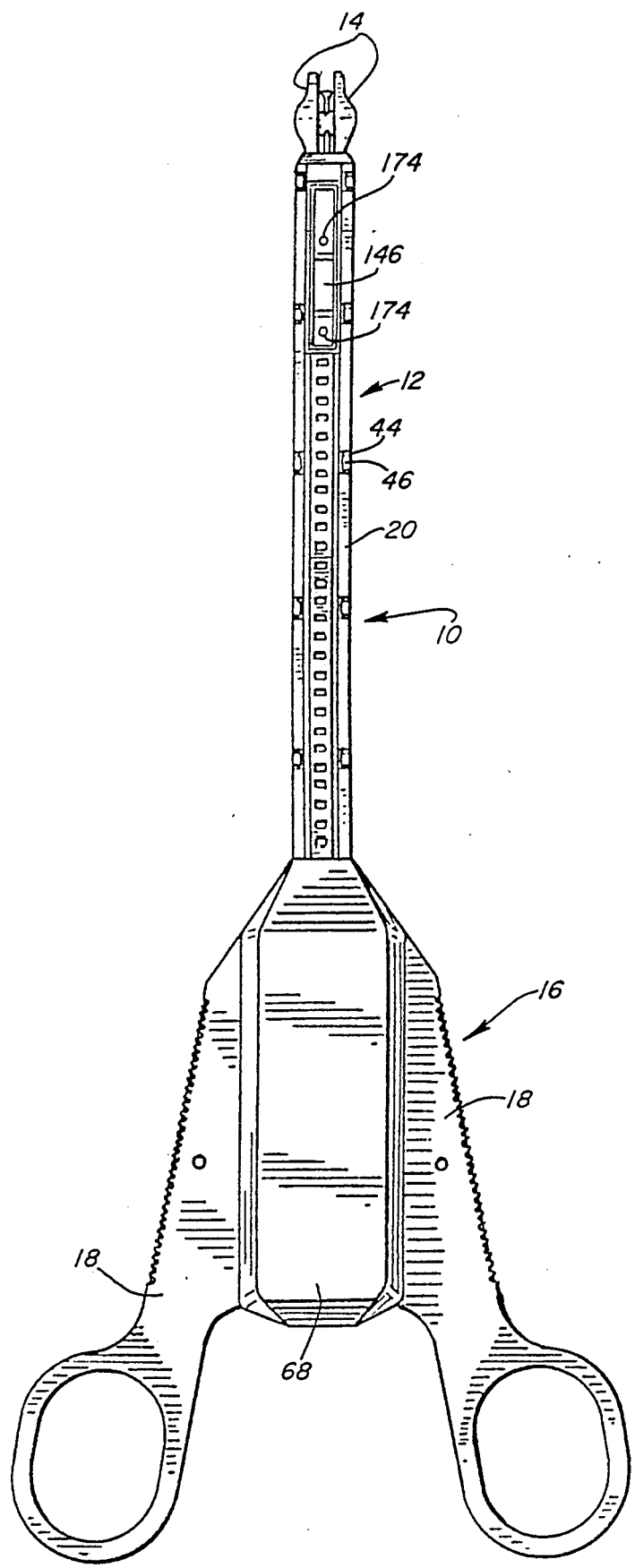
FIG. 17 is a top view of the hemostatic clip applier of the present invention.

Turning now to the drawings, the clip applicator 10 of the present invention, shown in FIG. 17, will be described. As can best be seen in FIGS. 1 and 12A, the clip applicator is provided with a forward operational end 12 which includes a pair of opposed jaws 14 for deforming surgical clips and a rearward actuating end 16 which includes a pair of handles 18. Operatively interconnected between the handles and the jaws is a clip housing or cartridge 20 which stores a supply of surgical clips and feeds a single clip to the jaws of the instrument for each complete actuation of the instrument.

In an unactuated state, a clip is positioned in the jaws ready for deformation about a blood vessel. In operation, the surgeon locates a blood vessel between the clip loaded in the jaws 14 and then completely closes the handles 18 causing the jaws 14 to deform the clip about the blood vessel. Upon opening of the handles 18 the next clip is fed to the jaws 14, and the instrument is ready to be activated again.

As is best seen in FIG. 1, the preferred embodiment of the applicator is provided with a chassis 22 which acts as the central supporting structure for the entire apparatus. The chassis 22 is a single unitary structure which runs the length of the instrument and provides both structural strength to the instrument and further improves the functioning of the instrument by insuring proper alignment of all other component members. The chassis 22 has an elongated channel shaped forward end 24 which contains and supports the clip housing or clip cartridge 20, a clip load platform member 26 for receiving the clips from the clip housing and for positioning the clips for entry into the jaws 14, a ram or clip advancer 28 for advancing the clips from the clip load platform 26 to the jaws 14 of the instrument, a pair of jaws 14, and a drawbar 30 interconnecting the jaws 14 to the actuating or transmission mechanism 32 of the instrument (FIG. 12A), and a tissue stop 34 for preventing a blood vessel from pushing a clip back into the instrument once the clip is loaded or positioned in the jaws of the instrument.

Described in more detail, the channel shaped forward end 24 of the chassis 22, shown in FIGS. 2 and 3, includes a base 36 and two sidewalls with a pair of internal shoulders 40 formed at the junction of the base and sidewalls. A camming member or anti-distortion ring is disposed at the distal end of the forward portion of the chassis and provides two opposed camming surfaces which act to cam the jaws closed. Additionally, the sidewalls 38 are provided with a series of upstanding tabs 44 which engage a series of cooperating slots 46 formed in the clip housing cover 50 to hold the forward end of the instrument together.

The rearward portion 41 of the chassis 22 is an extension of the base 36 of the elongated forward portion 24 and supports the transmission or actuating mechanism 32 of the present invention. The preferred embodiment of the transmission mechanism 32 is shown in FIGS. 1, 12 and 13 and comprises the handles 18, a drawbar extension 52 reciprocably mounted in a gear housing 54 and interconnected to the handles by a pair of links 56, a handle or trigger spring 58, an idler gear 60, a compound gear 62, a drawbar spring 64 and a lockout member 66. As shown in FIG. 1, the applicator is further provided with a cover plate 68 and a base plate 70 for enclosing and protecting these elements. Essentially, the transmission mechanism 32 translates the arcuate closure of the instrument handles 18 into linear movement and sequentially activates both the closing and opening of the jaws 14 and the advancing or feeding of the clips within the instrument.

For a more complete understanding of the instrument, the preferred embodiment will now be described with respect to its functional characteristics.

A. Clip Deformation

As previously stated, when the instrument is in an unactuated state a clip is loaded in the jaws 18 and the handles are completely open (FIGS. 4, 5 and 12A). As seen in FIG. 12B, upon closure of the handles 18, the drawbar extension 52 is caused to move rearwardly within the gear housing 54 as a result of its interconnection to the handles 18 by a pair of links 56. The handles 18 pivot about a pair of pivot pins 72, disposed on the bottom cover and extending through a pair of apertures 74 in the chassis 22. The pins 72 are engaged in a bore 75 formed at the forward end of the handles 18. Similarly, each link 56 is provided with an aperture 76 at each end to rotatably engage the upstanding pivots 78 at the rearward end of the drawbar extension 52 and to rotatably engage a link pin 80 mounted midway in the handle 18.

In the preferred embodiment, the links are attached to the jaw bar extension at separate, symmetric locations rather than being overlapped and attached to the drawback extension by a single pin. this latter, non-symmetric method of attachment creates a torque on the instrument during closure of the handles which attempts to turn the instrument in the surgeon's hand during use. Because of this design, the force acting on the instrument from opposite directions during closure of the handles balances and the instrument is more stable in the hand of the surgeon.

The drawbar extension 52 is essentially rectangular in shape and is provided with an elongated slot 82 which defines the interior sidewalls 84 and the interior endwalls 86 of the drawbar extension. As shown in FIGS. 15 and 16, the drawbar extension 52 is further provided with a pair of extensions or slide tabs to maintain the position and balance of the drawbar extension as it reciprocates within the gear housing 54. The first tab 88 extends downwardly from the bottom of the drawbar extension and slidably engages one sidewall 90 of the gear housing 54. The second tab 92 extends outwardly from the front end of the drawbar extension and slidably engages the upper surface of the other sidewall 94 of the gear housing (FIG. 12C). A third larger tab 96 or safety lug extends downwardly from the bottom of the drawbar extension near the interior rear end wall (FIG. 16) and cooperates with a lockout member (not shown) to prevent actuation of the instrument while a clip is being transferred from the clip housing 20 to the jaws 14.

The gear housing 54 is mounted to the rear portion of the chassis 22 by means well known in the art and is comprised of two sidewall portions 90 and 94 interconnected by a base plate 98 and an axle plate 100 (FIGS. 1, 15 and 16). Both the base plate 98 and the rear portion of the chassis are provided with cut out portions 102 and 104, respectively, to allow for the reciprocating movement of the drawbar safety lug 96. Each sidewall portion 90 or 94 is defined by a vertical wall 106 and 108, respectively, and a top surface 110 and 112, respectively, extending outwardly from the vertical wall with the left hand vertical 106 wall further provided with an inwardly extending slide tab 114. In operation, the drawbar extension 52 reciprocates between the vertical walls 106 and 108 of the gear housing 52. The first and second slide tabs 88 and 92 of the drawbar extension 52 and the slide tab 114 and base plate 98 of the gear housing 54 cooperate to maintain and slidably support the drawbar extension 52 during this movement.

A drawbar 30 is disposed in the forward end 24 of the chassis 22 and rests on top of the internal shoulders 40 (FIG. 1). During its rearward movement, the forward interior end wall 86F of the drawbar extension engages a pair of upstanding fingers 116 on the rear end of the drawbar thereby causing the drawbar 30 to move rearward in tandem with the drawbar extension 52 (FIG. 12B). In its rearward movement, the rear end of the drawbar maintains its elevated position with respect to the base 41 of the chassis 22 by sliding on an upwardly protruding nipple 120 formed in the base of the chassis (FIG. 1) and also by sliding on top of the ram or clip advancer 28 disposed beneath the drawbar 30 (FIG. 12C).

The jaws 14 of the instrument are interconnected to the forward end of the drawbar 30 by means of a pair of resilient or flexible jaw arms 122 (FIGS. 1 and 14) and upon rearward movement of the drawbar 30 the jaws 14 are also drawn rearward and ultimately cammed closed (FIGS. 4 and 6). The exterior edges of the jaws extend laterally outwardly to form a pair of camming surfaces 124. During the rearward movement of the jaws 18, these camming surfaces 124 contact a pair of inner surfaces 23 of the anti-distortion member or ring 25 (FIGS. 18 and 18a) located at the distal end of the forward portion 24 of the chassis 22 which cause the jaws to be cammed closed thereby deforming the forwardmost clip positioned in the jaws about a blood vessel. At this point (FIGS. 6 and 12C), the handles 18 will be completely closed and rearward movement of the jaws will be terminated.

The ring 25 acts against the camming surfaces 124 of the jaws 14 so that the jaws 14 are cammed closed to deform a clip positioned between the jaws (FIG. 8). In a device without the anti-distortion member 25, the continued action of the jaws 14 against the distal end of the chassis distorts the distal end of the chassis 22. Once the distal end becomes distorted, the jaws tend to rotate outward which causes the clips to form improperly. The addition of the anti-distortion ring 25 eliminates this problem.

Figure 18A:
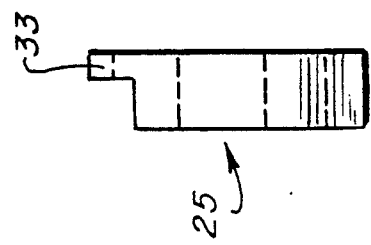
FIG. 18a is a side view of the anti-distortion member.
Figure 18:
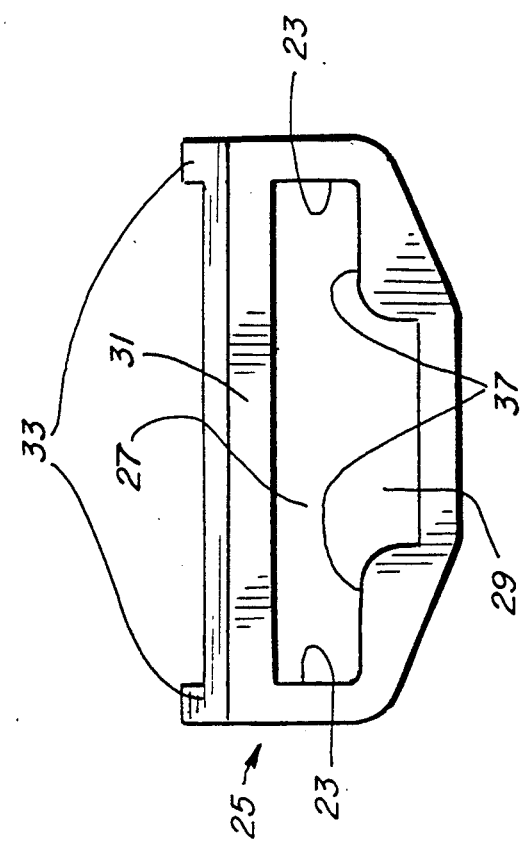
FIG. 18 is a front view of the anti-distortion member.

As can be seen in FIGS. 18 and 18a, a preferred embodiment of anti-distortion ring 25 is shown. The ring 25, positioned at the front end of the chassis 22, encloses both the jaws 14 and the clip load platform member 26. The jaws 14 fit within the upper-horizontal rectangular opening 27 and are cammed closed by inner surfaces 23. The ring is further provided with upstanding or vertical tabs 33 which fit within cooperating slots or cut-outs 35 in the clip housing cover 50 which secures the ring in position.

The ring is also provided with a cross member 31, shoulders 37, and inner surfaces 23, which maintain the alignment of the jaws during closure to limit undesirable rotation and misalignment of the individual jaw arms and jaws. The lower horizontal rectangular opening 29 allows the clip load platform member 26 to reciprocate in cooperation with the jaws.

Upon release of the handles 18 the instrument is caused to return to its unactuated position under the influence of the drawbar spring 64 and the handle spring 58 (FIGS. 1 and 13). The drawbar spring 64, disposed between the upstanding walls 126 formed in the bottom cover 70 of the instrument, is attached at its forward end to a downwardly depending finger 128 formed from the rear portion of the chassis 22 and at its rearward end to a downwardly depending finger 130 located at the rearward end of the drawbar. Both fingers are provided with notched ends to securely engage the spring. The finger 130 of the drawbar reciprocates in a slot 132 formed in the rearward portion of the chassis. The handle spring 58 extends between and interconnects the two handles 18. During closure of the instrument and deformation of a clip, the drawbar spring 64 is subject to tensioning and the handle spring 58 is subject to compression to thereby store energy in the springs. Upon release of the handles these two springs coact to open the handles 18 and to return the drawbar 30 and drawbar extension 52 to their forwardmost positions which thereby causes the jaws 18 to move forward and open as well. As will be discussed below, the forces supplied by these springs also act to advance and feed a clip to the jaws.

B. The Clip Housing

The dual level clip housing or cartridge 20 of the present invention is disposed along the forward elongate portion 24 of the chassis 22 and above the drawbar 30 and jaw arms 122 (FIG. 1). The clip housing 20 is comprised of a skirt 134 which is attached to the housing cover 50 to form a clip storage cavity 135. In particular, as seen in FIG. 1, the skirt 134 is provided with a pair of side walls 133. Multiple tabs 136 extending upwardly from the side walls 133 and have small apertures 138 formed therein which lockably engage multiple outwardly projecting knobs 140 formed in the receptive slots 46 spaced along the clip housing cover 50. In addition, the clip housing further comprises a ratchet advancer 142 which reciprocates within the skirt 134 and is interconnected to the drawbar 30 at its rearward end, a pawl 144 for advancing the clips within the clip housing and a pair of springs 146 disposed at the forward end of the housing cover 50 (FIGS. 5, 7, 9 and 11) for assisting in advancement of the clips to the jaws of the instrument. The ratchet advancer 142 is further provided with a forwardly extending nose or kicker 148.

Besides assisting in closing the jaws 14 of the instrument, the rearward movement of the drawbar 30 also actuates the mechanism for advancing the clips within the clip housing. The drawbar 30 is provided with a horizontal slot or opening 150 near its rearward end which engages a downwardly depending flange 152 affixed to the rearward end of the ratchet advancer 142. The ratchet advancer 142 slides on top of the skirt 134 member and is guided in its movement by a first pair of shoulders 154 formed in the clip housing cover (FIG. 3). The clips are abuttingly arranged in a continuous, forward facing line on top of the ratchet advancer 142 with the final rearwardmost clip engaged in the front portion of pawl 144 (FIG. 9). The housing cover 50 is further provided with a second pair of inwardly directed shoulders 155 for aligning and guiding the clips resting on the ratchet advancer 142 (FIG. 3). The ratchet advancer 142 is provided with a series of recesses or cutout portions 156 for engaging and advancing the pawl 144 (FIG. 1). The clip housing cover 50 is also provided with a ratchet surface 158 formed along the inside upper surface having cut out portions 160 for cooperating with the ratchet advancer 142 to engage and advance the pawl 144 (FIGS. 3 and 9).

Figure 21:
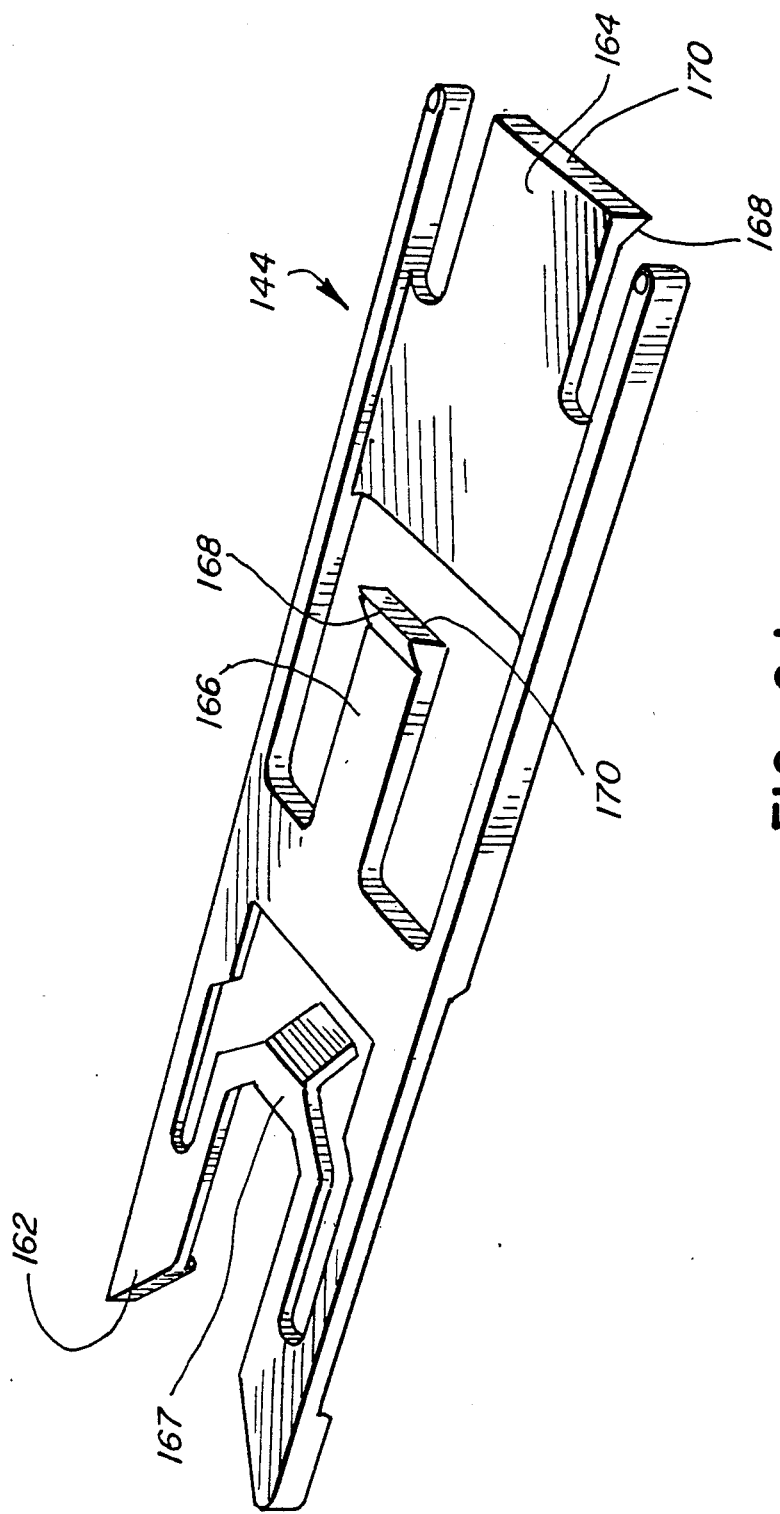
FIG. 21 is a perspective view of the pawl.

As can further be seen in FIG. 1, the pawl 144 is provided with a notched front end 162 adapted to receptively engage the rearward end or crown of the clips. Additionally, as shown in FIGS. 9 and 21, the pawl 144 is provided with a downwardly extending resilient flange 164 and an upwardly extending resilient flange 166 for engaging the cut out portions or recesses of the ratchet advancer 156 and the ratchet surface 158 of the housing cover 50, respectively. Each resilient flange is provided with a beveled forward surface 168 and a vertical rearward surface 170. The pawl 144 is activated by the reciprocating movement of the ratchet advancer 142. The flanges alternately engage and disengage the recesses of the ratchet advancer 142 and the ratchet surface 158 of the housing cover 50 to advance the clips in conjunction with the reciprocating motion of the ratchet advancer 142. The pawl also is provided with a final-lockout flange 167 which extends rearwardly from the front portion of the pawl to prevent actuation of the instrument after formation and release of the last clip.

As stated previously, the clip cartridge has two levels of clips. Besides being stored on the ratchet advancer 142, the preferred embodiment of the present invention places three or four clips on the skirt 134 in front of the ratchet advancer 142. The clip snap spring 172 is mounted on a pair of posts 174 on the clip housing cover 50 (FIG. 9) and assists in the transfer of clips from the ratchet advancer 142 to the skirt 134 or lower level. As shown in FIGS. 4 and 5, the skirt 134 terminates before reaching the internal forward wall 176 of the clip cover to thereby define a breach 178. The breach 178 provides the passage for the clips to be transferred from the skirt or lower level 134 to the jaws 14 of the instrument. By employing this multiple level clip feed arrangement, the forward end of the instrument can be provided with a small profile allowing the instrument to be operated in small areas.

As seen in FIGS. 4 and 5, the instrument is in an unactuated position with the forwardmost three clips on the skirt 134 and the fourth clip in transition from the ratchet advancer or upper level 142 to a position on the skirt or lower level 134.

In operation, FIGS. 1, 12, and 13, as the drawbar 30 moves rearwardly the engagement of the downwardly depending flange 152 of the ratchet advancer 142 with the cut out portion 150 of the drawbar 30 causes the ratchet advancer 142 to move rearwardly. Similarly, the clips resting on the ratchet advancer 142 are caused to be drawn rearwardly. However, rearward movement of the clips is prevented because the pawl 144 is prevented from moving rearwardly due to engagement of the vertical rearward edge 170 of the upwardly extending resilient flange 166 in the applicable recess of the ratchet surface 158 in housing cover 50. At the same time, the downwardly depending resilient flange 164 is caused to be cammed upwardly as the ratchet advancer 142 travels rearwardly due to the engagement of the beveled forward surface 168 of the downwardly depending resilient flange 164 with the forward edge of the applicable recess in the ratchet advancer 142. As a result, while the clips have not physically moved relative to the instrument, the clips have all moved forward on the ratchet advancer as a result of its rearward movement.

Figure 7:
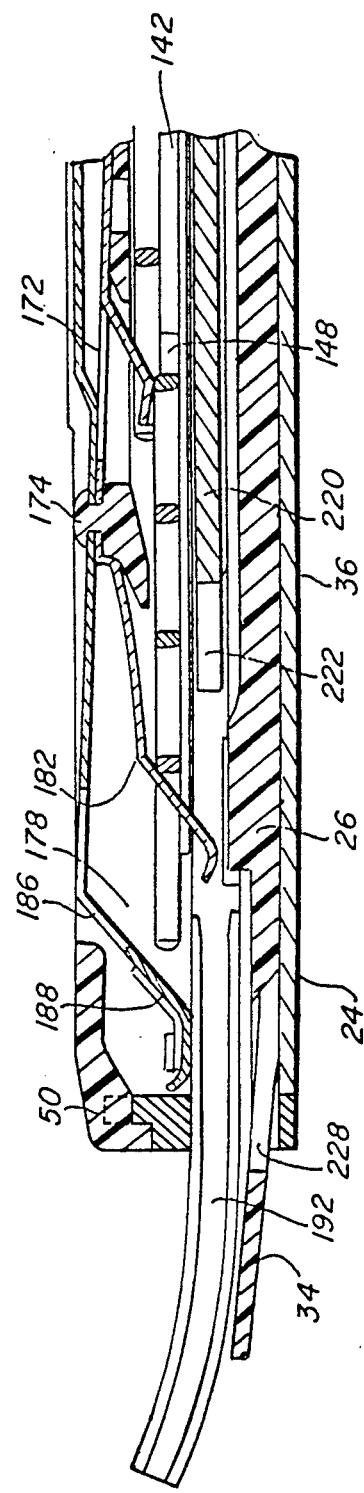
FIG. 7 is a side cross-sectional view of the present invention with the jaws in a fully closed position.

During this same rearward travel of the ratchet advancer 142, the forwardmost clip on the ratchet advancer is transferred from the ratchet advancer, FIGS. 4 and 5, to the upper surface of the skirt 134, FIGS. 6 and 7. As can be seen in FIG. 5, before the ratchet advancer 142 begins its rearward movement, the forwardmost clip on the ratchet advancer is already in transition to the skirt or lower level 134. This clip is positively held in transition between the rear tine 180 of the clip snap spring 172 and the kicker 148 extending from the front end of the ratchet advancer 142. As the ratchet advancer 142 retracts the kicker 148 ultimately is removed from beneath the clip and the clip snap spring 172 positions the clip on the skirt 134 while maintaining engagement with the crown or apex of the clip. (FIG. 7).

When the ratchet advancer 142 completes its rearward travel, the jaws are completely clinched and the kicker 148 is positioned immediately behind the last or rearwardmost clip on the skirt 134 (FIGS. 6 and 7). At this same point in the sequence of the instrument, the forwardmost clip on the skirt 134 is positively secured in position against the skirt by means of the front tine 182 of the clip snap spring 172 and prevents the clip from falling off the skirt and into the breach 178 of the jaws. In the preferred embodiment, four clips are position on the skirt at this point. It is certainly contemplated that fewer or more clips could be placed on this lower level, however, as the number of clips increases the effects of variations in clip length become more pronounced. The other clips are held in place by the shoulders 154 formed in the clip housing cover (FIG. 3). This allows the surgeon to maneuver and operate the instrument in various positions without risk of the clips moving or coming out of position and potentially jamming or fouling the instrument.

As the handles 18 are released, the drawbar 28 is caused to move forward under the influence of the drawbar spring 64 which, in turn, causes the ratchet advancer 142 to move forward as a result of their interconnection. Forward movement of the ratchet advancer 142 also drives the pawl 144 forward as the backwall of the appropriate ratchet advancer recess engages the vertical wall 170 of the downwardly depending flange 164 of the pawl 144. The forward movement of the pawl 144 relative to the stationary clip housing cover 50 causes the forward beveled surface 168 of the upwardly extending flange 166 of the pawl 144 to engage the applicable recess in the ratchet surface 158 of the clip housing cover 50 and be cammed downwardly thereby allowing the pawl 144 to move freely forward. The pawl 144 and recesses 156 and 160, respectively, formed in the ratchet advancer 142 and ratchet surface 158 of the clip housing cover 50 are designed in order that the pawl 144 advance one recess for each single actuation of the instrument. The resulting effect is that the clips on the ratchet advancer move forward one clip length as well.

Forward movement of the ratchet advancer 142 also causes the kicker 148 on the forward end of the ratchet advancer 142 to engage the crown or apex of the fourth clip on the skirt 134 and advance the four clips (FIGS. 8 and 9). As the forwardmost clip is pushed forward, the legs of the clip extend past the end of the skirt 134 and into the breach 178 above the clip load platform 26 and the crown or apex of the forwardmost clip causes the forward tine 180 of the clip snap spring 172 to deflect upwardly (FIG. 7).

Further forward movement causes the legs of the clip to contact the clip load spring 186 thereby forcing the clip downwardly toward the clip load platform 26

(FIG. 8 and 9). The clip load spring 186 in part overlies the clip snap spring 172 and is mounted to the clip cover 50 on the same pair of posts 174 as the clip snap spring 172 (FIG. 9). As best seen in FIGS. 2 and 14, the tine 188 of the clip load spring 186 is provided with a pair of stepped laterally extending members interconnected by a pair of outwardly slanted segments. The uppermost laterally extending surfaces 190 abut the top of the jaw 122 arms and prevent the clip load spring 186 from overpowering the clip load platform 26 and forcing the clip below the clip tracks 192 formed in the jaws channels. These uppermost outwardly extending lateral surfaces also act as safety features to prevent the clip load spring from becoming trapped between the jaw arms 122 to prevent closure of the jaws.

The intermediate laterally extending surfaces 194 and the first pair of outwardly slanted surfaces 196 create a first recess for engaging the legs of a clip. As seen in FIGS. 2 and 14, this first recess horizontally centers the clip on the clip load platform 26. Moreover, as the jaw arms 122 close the outwardly slanted segments 196 cause the clip load spring 186 to be cammed upwardly out of the way of the closing jaws arm 122.

Figure 10:
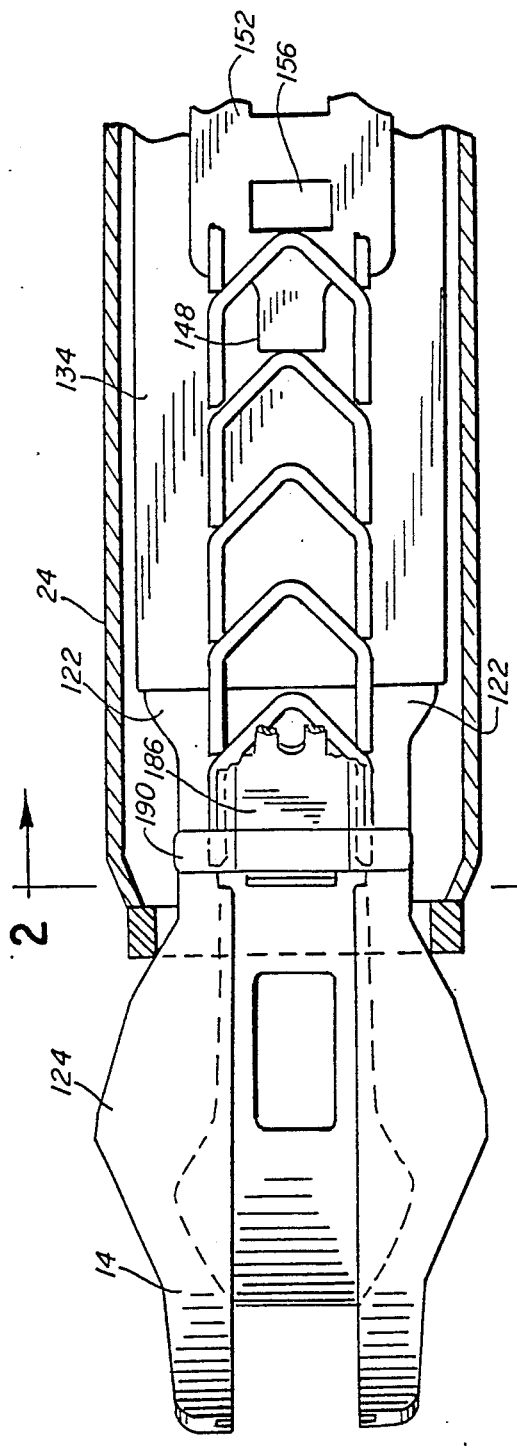
FIG. 10 is a partial top view of the instrument shown in FIG. 11.
Figure 11:
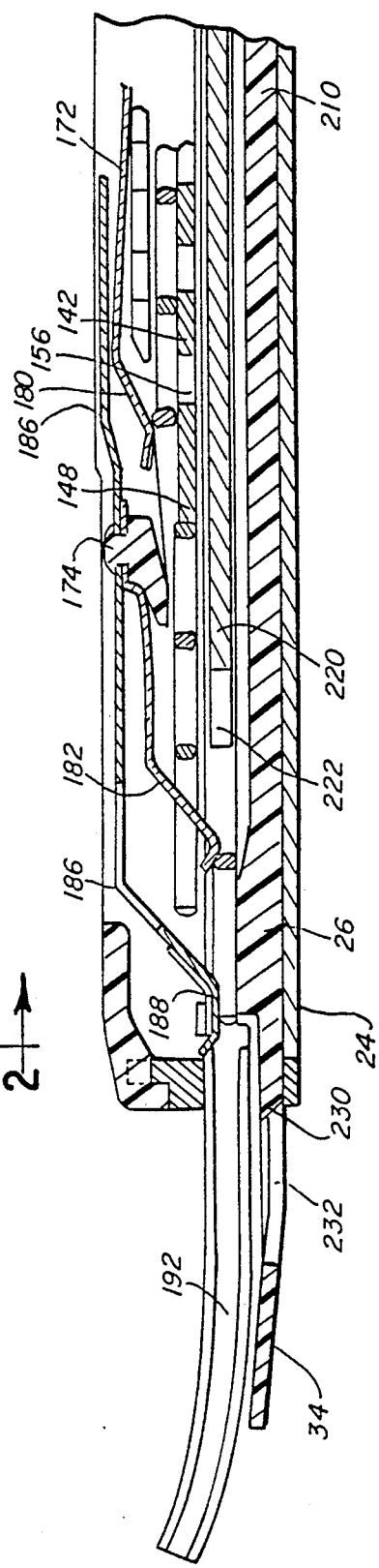
FIG. 11 is a side cross-sectional view of the present invention returning to the at rest position with the jaws fully open and the forwardmost clip on the clip load platform.

More specifically, the forwardmost clip is engaged at three points, FIG. 9, and as it is advanced over the edge of the skirt 134, the legs of the clip are first driven downwardly by the clip load spring 186 and subsequently, after the clip has been pushed off the skirt 134 and fully into the breach 178, the crown apex of the clip is driven downwardly by the front tine 180 of the clip snap spring 172 until the clip is positioned on the clip load platform 26 (FIGS. 10 and 11). The positive coaction of the clip load spring 186 and clip snap spring 172 in driving the clip to the clip load platform 26 allows the instrument to be operated in any position without fear of the clip being misfed due to gravity or other negative factors. Moreover, the opposing actions of the clip load spring 186 and the resilient clip load platform 26 act to position or align the clip with the clip tracks 192 formed in the jaws 14 (FIG. 14) for subsequent advancement of the clip to the jaws.

C. Positioning The Clip In The Jaws

As can be seen in FIG. 14, the jaws 14 of the instrument are provided with a track or channel 192 for guiding the clip between the jaws and for positioning and holding the clip during the deformation. It is important that a clip be properly positioned or aligned prior to entry into the tracks 192 in order to avoid the clip becoming jammed or misfed as it slides to the forward part of the jaws. Consequently, the clip load platform 26 is positioned to counterbalance the downward action of the clip load spring 186 and clip snap spring 172. Both the clip load platform 26 and clip load spring 186 are designed to center the clip both vertically and horizontally for proper alignment with the clip tracks 192.

The clip is moved from the clip load platform 26 to the jaws 14 of the instrument by means of a reciprocating ram or clip advancer 28. The ram 28 is an elongated member with a gear rack 216 disposed at its rearward end and a pair of spaced extension arms 218 at its front end (FIG. 1). As is best shown in FIG. 1, a clip engaging member 220 is mounted on top of the extension arms 218 and extends forward therefrom and terminates in a notched front end 222 for engaging the apex or crown of a clip. The ram reciprocates along the base 36 of the forward end 24 of the chassis 22 between the opposed shoulders 40 as shown in FIG. 3. The slot 224 formed between the extension arms 218 allows the ram to reciprocate without interfering with the engagement of the clip stop platform guidepost 212 with the drawbar 30.

As shown in FIGS. 4 and 5, the instrument is in the fully open position and the ram 28 is abutting the apex or crown of the clip. When the instrument is unactuated, the ram 28 functions as the clip stop to prevent the clip from being forced back into the instrument. Such an occurrence could happen merely by gravity or when a surgeon moves the instrument forward after placing the clip about a blood vessel. This forward movement of the instrument in conjunction with the stationary position of the blood vessel causes the blood vessel to force the clip back into the instrument potentially causing a jam and certainly causing delay and frustration in the surgical procedure while the errant clip is retrieved.

However, in the present invention the ram 28 cannot remain in its forward position during actuation of the instrument. The presence of the ram would prevent the jaws 18 from completely closing and this would prevent the clip from being completely clenched about the blood vessel. Consequently, the instrument provides for the ram to be withdrawn rearwardly into the instrument before the jaws are closed. Because removal of the ram leaves the clip without a clip stop, a tissue or vessel stop 34 is incorporated at the distal end of the clip load platform 26 to function in place of the ram 28 during closure of the jaws in the absence of the ram 28 to prevent a tissue or blood vessel from pushing a clip into the instrument.

As best shown in FIGS. 14 and 14A, the tissue stop 34 is positioned beneath the jaws 14 of the instrument and has two lateral extensions 226 which allow the tissue stop 34 to span the open jaws 14 and prevent the tissue stop from being caught between the instrument jaws.

While it is intended that every clip will be properly formed about a blood vessel, it is realized that the present invention will be operated or tested prior to use in surgery or simply by potential purchasers in an environment without vessels or tissue for the clips to be clamped around. As a result, the deformed clips will be unattached to any stationary object and, therefore, free to possibly fall or slide into the instrument and cause a jam. To remove this remote possibility, the tissue or vessel stop is further provided with a rectangular hole 228 in the base 229 and a raised, forwardly slanting tooth 230 at the back side of this hole (FIG. 14A). The tooth 230 is an extension of the extension arm or center rib 210 of the clip load platform 26. In addition, the side edges of the clip load platform are raised to create shoulders or side walls 232 on the clip load platform base 229. Consequently, if the instrument was actuated without a vessel or tissue, the deformed clip will slide down the base 229 of the clip load platform 26 guided by the outside shoulders 232 and would fall harmlessly through the hole 228 either before or after striking the raised tooth 230 at the back end of the hole. The forward slant of the tooth 230 acts to direct the clip downward.

D. The Final Lock-Out Mechanism

The present invention is also provided with a final lock-out mechanism which prevents actuation of the instrument after the last clip has been formed and released from the jaws. The final lock-out mechanism results from the action of the final-lockout flange 167 of pawl 144 which prevents ram 28 from moving forward and jaws 14 from being cammed closed when there are no more clips to be formed. Without this feature, the instrument would still actuate and the jaws could be closed around an artery or blood vessel possibly damaging or even severing the vessel.

Figure 19:
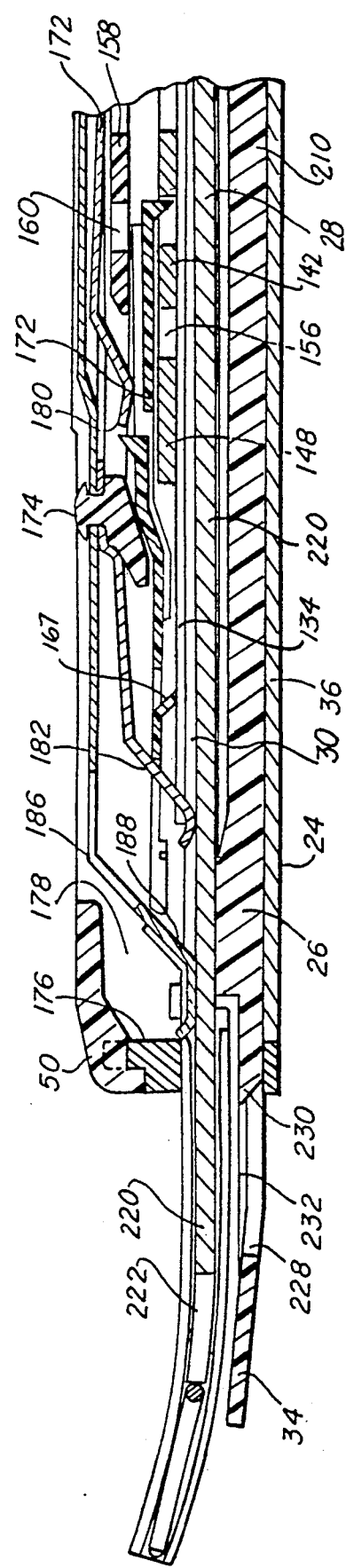
FIG. 19 is a side cross-sectional view of the present invention with the last clip positioned in the jaws and ready for formation.

FIG. 19 illustrates the location of the pawl 144 when the last clip is being formed. At this point the pawl 144 has been advanced forward so that tine 182 of clip snap spring 172 rests inside of notched front end 162.

Figure 20:
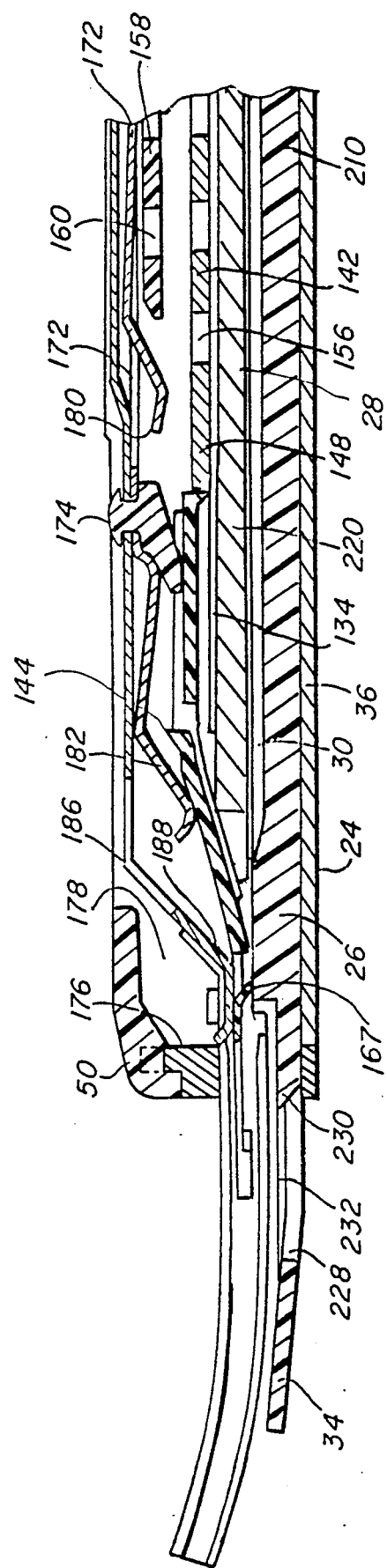
FIG. 20 is a side cross-sectional view after the last clip has been formed and released from the instrument.

After the last clip has been formed and released from the instrument, the rear half of pawl 144 is positioned on top of the skirt 134 (FIG. 20), and the front half of pawl 144 is positioned in the clip tracks 192 by the action of the tine 188 of clip load spring 186. The final lockout flange 167 is now positioned to block the forward extension of the ram 28. Thus, as the handles of the instrument are closed, the forward movement of ram 28 is stopped by final lockout flange 167. Since ram 28 cannot move forward, jaws 14 are prevented from closing. This action keeps jaws 14 from closing fully upon an artery, thereby preventing an artery from being damaged or even severed.

Whereas a preferred embodiment and certain alternative designs have been shown and described herein, it will be apparent that other modifications, alterations and variations may be made by and will occur to those skilled in the art to which this invention pertains, particularly upon considering the foregoing teachings. For example, the forward clip engaging end of the clip load spring may be comprise a center tine having only a single pair of laterally extending members interconnected by a single pair of outwardly slanted segments. A spring of this shape would also act to align the clips upon transfer to the clip load platform. In addition, it is contemplated that a clip stop may be affixed to the forward end of the tissue stop to prevent rearward movement of the clips after retraction of the ram or clip advancer. It is, therefore, contemplated by the appended claims to cover any such modifications and other embodiments as incorporated those features which constitute the essential features of this invention within the true spirit and scope of the following claims.

What is claimed is:

1. In an apparatus for applying surgical clips, having a pair of opposed spaced jaws, a main body including clip housing and feed means for storing and advancing clips to the jaws, and transmission means associated with the body to actuate the clip feed means and associated with the jaws to cam the jaws against the forward end of the main body to effectuate closure of the jaws and deform a clip disposed therebetween, the improvement comprising:

an anti-distortion means associated with the forward end of the main body for preventing distortion of the forward end of the main body and for preventing rotation and misalignment of the jaws during clip closure, said anti-distortion means including means for camming the jaws at the outer edges of the jaws and means for aligning at the tope and bottom of the jaws.

2. In an apparatus for applying surgical clips as defined in claim 1, wherein the improvement further comprises said means for camming includes a pair of inner surface means for providing contact with the outer edges of the jaw to deform the clip disposed therebetween.

3. In an apparatus for applying surgical clips as defined in claim 1, wherein the improvement further comprises said anti-distortion means comprises at least one piece.

4. In an apparatus for applying surgical clips as defined in claim 2, wherein said improvement further comprises said means for aligning includes a pair of shoulder means for acting in cooperation with said pair of inner surface means to maintain the alignment of the jaws during closure thereby limiting undesirable rotation and misalignment of the jaws.

5. An apparatus for applying surgical clips comprising a substantially rectilinear housing having a forward and rearward end and a top member and a bottom member defining substantially open sides, a pair of handles disposed along said open sides and rotatably affixed to said rearward end of said housing, said handles movable between a first open position wherein said housing and handles are substantially V-shaped, and a second position wherein said handles are substantially incorporated into said housing, an elongate nose portion extending from said forward end of said housing and terminating with a pair of opposed spaced jaws for deforming a clip about a blood vessel and an anti-distortion means associated with said forward end of said housing for preventing distortion of said forward end of said housing and for preventing rotation and misalignment of the jaws during clip closure, said anti-distortion means including means for camming the jaws at the outer edges of the jaws and means for aligning at the top and bottom of the jaws.

6. An apparatus for applying surgical clips are defined in claim 5 wherein said means for camming includes a pair of inner surface means for providing contact with the outer edges of the jaws, thereby deforming the clip disposed therebetween.

7. An apparatus for applying surgical clips as defined in claim 5 wherein said anti-distortion means comprises at least one piece.

8. An apparatus for applying surgical clips as defined in claim 5 wherein said means for aligning includes a pair of shoulder means for acting in cooperation with said pair of inner surface means to maintain the alignment of the jaws during closure thereby limiting undesirable rotation and misalignment of the jaws.

9. An apparatus for applying hemostatic clips to blood vessels, arteries, veins, tissue or the like to occlude the flow of blood, and apparatus comprising:

A. a chassis running the length of the apparatus and having an elongate front portion and a rear portion;

B. a pair of opposed jaws associated with the distal end of said elongate portion of said chassis and having a clip track formed therein for receiving and deforming a clip about a vessel;

C. an anti-distortion means associated with said front portion of said chassis for preventing distortion of said forward portion of said chassis and for preventing rotation and misalignment of said jaws during clip closure, said anti-distortion means including means for camming said jaws at the outer edges of said jaws and means for aligning at the top and bottom of the jaws.

D. actuating means mounted on said rear portion of said chassis, said actuating means movable between a first position and a second position;

E. clip housing and feed means mounted to said chassis and associated with said jaws to store a plurality of hemostatic clips and to serially advance the clips one at a time to said jaws, said clip housing and feed means comprising a clip housing defining a clip storage cavity having an upper level and a lower level, said upper and lower levels adapted to hold a plurality of clips abuttingly arranged in a single forward facing row, said upper level communicating with said lower level to transfer a single clip to said lower level upon movement of said actuation means from said first position to said second position and a resilient clip load platform means subtending and communicating with said clip housing, said clip load platform means adapted to receive a single clip from said clip housing upon movement of said actuation means from said second position to said first position wherein said upper level of said clip storage cavity comprises a first ratchet surface fixably secured to said chassis, a second ratchet surface operatively coupled to said transmission means and adapted to move in a reciprocating forward and rearward motion, and pawl means for serially advancing the clips disposed between said first and second ratchet surfaces, said pawl means having engagement means for alternately engaging said second ratchet surface as said second ratchet surface moves forward such that said pawl means is moved forward with said second ratchet surface, and for engaging said first ratchet surface as said second ratchet surface moves rearward to prevent rearward movement of said pawl means and for keeping said jaws from closing one the last clip has been used; and F. transmission means operatively interconnecting said jaws, said actuating means and said clip housing and feed means such that upon movement of said actuating means from said first position to said second position said jaws are caused to move rearward with respect to said chassis and be cammed closed by said anti-distortion means to deform a clip positioned between said jaws, and upon movement of said actuating means from said second position to said first position said jaws are caused to move forward with respect to said chassis and to open, and said clip housing and feed means are caused to feed a clip to said jaws.

10. An apparatus for applying hemostatic clips to blood vessels, arteries, veins, tissue or the like to occlude the flow of blood, as defined in claim 9 wherein said means for camming includes a pair of inner surface means for providing contact with the outer edges of the jaws to deform the clip disposed therebetween.

11. An apparatus for applying hemostatic clips to blood vessels, arteries, veins, tissue or the like to occlude the flow of blood, as defined in claim 10 wherein said anti-distortion means comprise at least one piece.

12. An apparatus for applying hemostatic clips as defined in claim 11 wherein means for aligning includes a pair of shoulder means for acting in cooperation with said pair of inner surface means to maintain the alignment of the jaws during closure thereby limiting undesirable rotation and misalignment of the jaws.

13. An apparatus for applying hemostatic clips to blood vessels, arteries, veins, tissue or the like to occlude the flow of blood, said apparatus comprising:

A. a chassis running the length of the apparatus and having an elongate front portion and a rear portion;

B. a pair of opposed jaws associated with the distal end of said elongate portion of said chassis and having a clip track formed therein for receiving and deforming a clip about a vessel;

C. an anti-distortion means associated with said front portion of said chassis for preventing distortion of said portion of said chassis and for preventing rotation and misalignment of said jaws during clip closure, said anti-distortion means including means for camming said jaws at the outer edges of said jaws and means for aligning at the top and bottom of said jaws, D. actuating means mounted of said rear portion of said chassis, said actuating means movable between a first position and a second position;

E. clip housing and feed means mounted to said chassis and associated with said jaws to serially advance the clips one at a time to said jaws, said clip housing and feed means comprising a clip housing adapted to hold a plurality of clips abuttingly arranged in a forward facing row and a resilient clip load platform means subtending and communicating with said clip housing, said clip load platform means adapted to supportingly receive a single clip form said clip housing upon movement of said actuation means from said second position to said first position wherein said clip housing has an upper level and a lower level, said upper and lower levels adapted to hold a plurality of clips abuttingly arranged in a forward facing row, said upper level communicating with said lower level to transfer a single clip to said lower level upon movement of said actuation means from said first position to said second position wherein said upper level of said clip storage cavity comprises a first ratchet surface fixably secured to said chassis, a second ratchet surface operatively coupled to said transmission means and adapted to move in a reciprocating forward and rearward motion, and pawl means for serially advancing the clips disposed between said first and second ratchet surfaces, said pawl means having engagement means for alternately engaging said second ratchet surfaces, said pawl means having engagement means for alternately engaging said second ratchet surface as said second ratchet surface moves forward such that said pawl means is moved forward with said second ratchet surface, and for engaging said first ratchet surface as said second ratchet surface moves rearward to prevent rearward movement of said pawl means, and for keeping said pair of opposed jaws from closing once the last clip has used; and F. transmissions means operatively interconnecting said jaws, said actuating means and said clip housing and feed means such that upon movement of said actuating means from said first position to said second position said jaws are caused to move rearward with respect to said chassis and be cammed closed by said anti-distortion means to deform a clip positioned between said jaws, and upon movement of said actuating means from said second position to said first position said jaws are caused to move forward with respect to said chassis and to open, and said clip housing and feed means is caused to fee a clip to said jaws.

14. An apparatus for applying hemostatic clips to blood vessels, arteries, veins, tissue or the like to occlude the flow of blood, as defined in claim 13, wherein said means for camming includes a pair of inner surface means for providing contact with the outer edges of the jaws to deform the clip disposed therebetween.

15. An apparatus for applying hemostatic clips to blood vessels, arteries, veins, tissue or the like to occlude the flow of blood, as defined in claim 14, wherein said anti-distortion means comprises at least one piece.

16. An apparatus for applying hemostatic clips as defined in claim 14, wherein said means for aligning further includes a pair of shoulder means for acting in cooperation with said pair of inner surface means to maintain the alignment of the jaws during closure thereby limiting undesirable rotation and misalignment of the jaws.

17. In an apparatus for applying surgical clips, having a pair of opposed spaced jaws, a main body including clip housing and clip feed means for storing and advancing clips to the jaws, and transmission means associated with the body to actuate the clip feed means and to close the jaws and deform a clip disposed therebetween, said clip feed means including ram means for advancing said clips into said jaws, the improvement comprising:

a lockout means associated with said clip housing means and said clip feed means, said lockout means being forced into the jaws by said clip feed means, to prevent said ram means from moving forward thereby preventing the jaws from closing after the last clip has been used, said lockout means comprising final lockout flange means for blocking the forward advance of said ram means thereby preventing the closure of the jaws and notched front end means for receptively engaging the rearward end of said clips.

18. In an apparatus for applying surgical clips as defined in claim 16, wherein the improvement further comprises said lockout means further including downwardly extending resilient flange means and upwardly extending resilient flange means for engaging said clip feed means to advance said clips.

19. In an apparatus for applying surgical clips, having a pair of opposed spaced jaws, a main body including clip housing and feed means for storing and advancing clips to the jaw, and transmission means associated with the body to actuate the clip feed means and associated with the jaws to cam the jaws against the forward end of the main body to effectuate closure of the jaws and deform a clip disposed therebetween, the improvement comprising:

an anti-distortion member associated with the forward end of the main body to prevent distortion of the forward end of the main body due to the camming action of the pair of opposed jaws on the forward end of the main body, said anti-distortion member including a pair of inner surface means for camming the pair of jaws closed to deform the clip disposed therebetween and a pair of shoulder means for acting in cooperation with said pair of inner surface means to maintain the alignment of the jaws during closure thereby limiting undesirable rotation and misalignment of the jaws.

20. An apparatus for applying surgical clips comprising a substantially rectilinear housing having a forward and rearward end and a top member and a bottom member defining substantially open sides, a pair of handles disposed along said open sides and rotatably affixed to said rearward end of said housing, said handles movable between a first open position wherein said housing and handles are substantially V-shaped, and a second position wherein said handles are substantially incorporated into said housing, an elongate nose portion extending from said forward end of said housing and terminating with a pair of opposed spaced jaws for deforming a clip about a blood vessel and an anti-distortion member encircling said forward end of said housing, said anti-distortion member comprising a pair of inner surface means for camming the pair of jaws closed to deform the clip disposed therebetween and a pair of shoulder means for acting in cooperation with said pair of inner surface means to maintain the alignment of the jaws during closure thereby limiting undesirable rotation and misalignment of the jaws.

21. An apparatus for applying hemostatic clips to blood vessels, arteries, veins, tissue or the like to occlude the flow of blood, and apparatus comprising:

A. a chassis running the length of the apparatus and having an elongate front portion and a rear portion;

B. a pair of opposed jaws associated with the distal end of said elongate portion of said chassis and having a clip track formed therein for receiving and deforming a clip about a vessel;

C. an anti-distortion member associated with said front portion of said chassis to effectuate closure of said jaws, said anti-distortion member comprising a pair of inner surface means for camming the pair of jaws closed to deform the clip disposed therebetween and a pair of shoulder means for acting in cooperation with said pair of inner surface means to maintain the alignment of the jaws during closure thereby limiting undesirable rotation and misalignment of the jaws;

D. actuating means mounted on said rear portion of said chassis, said actuating means movable between a first position and a second position;

E. clip housing and feed means mounted to said chassis and associated with said jaws to store a plurality of hemostatic clips and to serially advance the clips one at a time to said jaws, said clip housing and feed means comprising a clip housing defining a clip storage cavity having an upper level and a lower level, said upper and lower levels adapted to hold a plurality of clips abuttingly arranged in a single forward facing row, said upper level communicating with said lower level to transfer a single clip to said lower level upon movement of said actuation means from said first position to said second position and a resilient clip load platform means subtending and communicating with said clip housing, said clip load platform means adapted to receive a single clip from said clip housing upon movement of said actuation means from said second position to said first position wherein said upper level of said clip storage cavity comprises a first ratchet surface fixably secured to said chassis, a second ratchet surface operatively coupled to said transmission means and adapted to move in a reciprocating forward and rearward position, and pawl means for serially advancing the clips disposed between said first and second ratchet surfaces, said pawl means having engagement means for alternately engaging said second ratchet surface as said second ratchet surface moves forward such that said pawl means is moved forward with said second ratchet surface, and for engaging said first ratchet surface as said second ratchet surface moves rearward to prevent rearward movement of said pawl means and for keeping said jaws from closing once the last clip has been used; and F. transmission means operatively interconnecting said jaws, said actuating means and said clip housing and feed means such that upon movement of said actuating means from said first position to said second position said jaws are caused to move rearward with respect to said chassis and be cammed closed by said anti-distortion member to deform a clip positioned between said jaws, and upon movement of said actuating means from said second position to said first position said jaws are caused to move forward with respect to said chassis and to open, and said clip housing and feed means are caused to feed a clip to said jaws.

22. An apparatus for applying hemostatic clips to blood vessels, arteries, veins, tissue or the like to occlude the flow of blood, said apparatus comprising:
  A. a chassis running the length of the apparatus and having an elongate front portion and a rear portion;
  B. a pair of opposed jaws associated with the distal end of said elongate portion of said chassis and having a clip track formed therein for receiving and deforming a clip about a vessel;
  C. an anti-distortion member associated with said front portion of said chassis to effectuate closure of said jaws, said anti-distortion member comprising a pair of inner surface means for camming the pair of jaws closed to deform the clip disposed therebetween and a pair of shoulder means for acting in cooperation with said pair of inner surface means to maintain the alignment of the jaws during closure thereby limiting undesirable rotation and misalignment of the jaws;
  D. actuating means mounted on said rear portion of said chassis, said actuating means movable between a first position and a second position;
  E. clip housing and feed means mounted to said chassis and associated with said jaws to serially advance the clips one at a time to said jaws, said clip housing and feed means comprising a clip housing adapted to hold a plurality of clips abuttingly arranged in a forward facing row and a resilient clip load platform means subtending and communicating with said clip housing, said clip load platform means adapted to supportingly receive a single clip from said clip housing upon movement of said actuation means from said second position to said first position wherein said clip housing has an upper level and a lower level, said upper and lower levels adapted to hold a plurality of clips abuttingly arrange din a forward facing row, said upper level communicating with said lower level to transfer a single clip to said lower level upon movement of said actuation means from said first position to said second position wherein said upper level of said clip storage cavity comprises a first ratchet surface fixably secured to said chassis, a second ratchet surface operatively coupled to said transmission means and adapted to move in a reciprocating forward and rearward motion, and pawl means for serially advancing the clips disposed between said first and second ratchet surfaces, said pawl means having engagement means for alternately engaging said second ratchet surfaces, said pawl means having engagement means for alternately engaging said second ratchet surface as said second ratchet surface moves forward such that said pawl means is moved forward with said second ratchet surface, and for moves rearward to prevent rearward movement of said pawl means, and for keeping said pair of opposed jaws from closing once the last clip has used; and
  F. transmission means operatively interconnecting said jaws, said actuating means and said clip housing and feed means such that upon movement of said actuating means from said first position to said second position said jaws are caused to move rearward with respect to said chassis and be cammed closed by said anti-distortion member to deform a clip positioned between said jaws, and upon movement of said actuating means from said second position to said first position said jaws are caused to move forward with respect to said chassis and to open, and said clip housing and feed means is caused to feed a clip to said jaws.

* * * * *

UNITED STATES PATENT AND TRADEMARK OFFICE
CERTIFICATE OF CORRECTION

PATENT NO. : 5,049,152

DATED : September 17, 1991

INVENTOR(S) : Denise M. Simon, et al

It is certified that error appears in the above-identified patent and that said Letters Patent is hereby corrected as shown below:

Column 6, line 28 in the word "this" the t should be -- T --;

Column 11, line 11 before the word "clip" delete -- . --;

Col. 13, claim 1, line 59 delete the word "tope" and substitute therefor -- top --;

Col. 17, claim 18, line 32 delete "16" and substitute therefor --17--;

Col. 20, claim 22, lines 5 and 6 delete "ar-range din" and substitute therefor -- arranged in --; and Col. 20, claim 22, line 24 after the word "for" add --engaging said first ratchet surface as said second ratchet surface --.

Signed and Sealed this

Thirtieth Day of March, 1993

Attest:

STEPHEN G. KUNIN

*Attesting Officer*     *Acting Commissioner of Patents and Trademarks*